United States Patent
Clark et al.

(10) Patent No.: US 8,980,639 B2
(45) Date of Patent: Mar. 17, 2015

(54) OXIDATION STATE SENSORS AND METHODS FOR TRANSITION METAL ALLOYS

(75) Inventors: Daniel Clark, Derbyshire (GB); Justin Burrows, Derbyshire (GB)

(73) Assignee: Rolls-Royce PLC, London (GB)

( * ) Notice: Subject to any disclaimer, the term of this patent is extended or adjusted under 35 U.S.C. 154(b) by 53 days.

(21) Appl. No.: 13/265,158

(22) PCT Filed: Apr. 16, 2010

(86) PCT No.: PCT/GB2010/000769
§ 371 (c)(1),
(2), (4) Date: Oct. 19, 2011

(87) PCT Pub. No.: WO2010/122287
PCT Pub. Date: Oct. 28, 2010

(65) Prior Publication Data
US 2012/0040467 A1    Feb. 16, 2012

(30) Foreign Application Priority Data
Apr. 24, 2009 (GB) .................................. 0907110.1

(51) Int. Cl.
*G01N 33/20* (2006.01)
*G01N 21/76* (2006.01)
(Continued)

(52) U.S. Cl.
CPC ............. *G01N 21/643* (2013.01); *G01N 21/91* (2013.01); *G01N 31/22* (2013.01)
USPC ................. 436/80; 436/73; 436/84; 436/164; 436/172

(58) Field of Classification Search
CPC ... G01N 31/22; G01N 33/20; G01N 33/1813; G01N 33/84; G01N 21/78; G01N 21/29; C02F 1/72; C02F 11/086; A61K 31/295; A61K 31/2016; A61K 33/26
USPC .................................... 436/80, 73, 84, 6, 164
See application file for complete search history.

(56) References Cited

U.S. PATENT DOCUMENTS 2,963,349 A   12/1960   Bernard et al.
5,648,270 A    7/1997   Kuhn et al.
(Continued)

FOREIGN PATENT DOCUMENTS

EP    2 003 439 A1   12/2008
GB    2 434 447 A     7/2007
(Continued)

OTHER PUBLICATIONS

Buchler et al., "Fluorescence and Near-Field Scanning Optical Microscopy for Investigation Initiation of Localized Corrosion of Al 2024", Journal of the Electrochemical Society, 147 (10), 2000, pp. 3691-3699.

(Continued)

*Primary Examiner* — Krishnan S Menon
*Assistant Examiner* — Dwan A Gerido
(74) *Attorney, Agent, or Firm* — Woodard, Emhardt, Moriarty, McNett & Henry LLP (57) ABSTRACT

The present invention is concerned with a method of discriminating between, in a surface of a transition metal alloy, transition metals in different oxidation states using surface sensor molecules adapted to associate selectively with one of the transition metals. In particular, the present invention provides a method of identifying degradation in aircraft components such as turbine blades, engine casings and aerofoils. In embodiments, a surface sensor molecule comprising an oxidation state discriminating group, such as an imidazole, and a fluorescein probe is applied in aqueous solution to the surface of a service-run Ni alloy aircraft component. The sensor molecule selectively associates with transition metals in oxidation states greater than zero such that fluorescence imaging can be used to identify areas of degradation.

22 Claims, 3 Drawing Sheets

(51) Int. Cl.
*G01N 21/64* (2006.01)
*G01N 31/22* (2006.01)
*G01N 21/91* (2006.01)

(56) References Cited

U.S. PATENT DOCUMENTS 6,146,842 A   11/2000  Josiah et al.
8,623,653 B2 *  1/2014  Lalgudi et al. .................... 436/6
2003/0068824 A1  4/2003  Frankel et al.

FOREIGN PATENT DOCUMENTS

| JP | 56166454 | 12/1981 |
| WO | WO 00/08461 | 2/2000 |
| WO | WO 2007/025107 A2 | 3/2007 |

OTHER PUBLICATIONS

United Kingdom International Search and Examination Report, GB Application No. 0907110.1, Aug. 21, 2009, 8 pps.
Agarwal et al., "Immobilization of Histidine-Tagged Proteins on Nickel by Electrochemical Dip Pen Nanolithography", Journal of the American Chemical Society, 125(24), 2003, 7408-7412.
Aggarwal et al., "An Oxide of Tervalent Nickel", Journal of Physical Chemistry, 65(11), 1961, 2105.
Chen et al., "The electrochromic properties of nickel oxide by chemical deposition and oxidation", Materials Letters, 60(6), 2006, 790-795.
Figueroa et al., "High-Performance Immobilized-Metal Affinity Chromatography of Proteins of Iminodiacetic Acid Silica-Based Bonded Phases", Journal of Chromatography, 371, 1986, 335-352.
Gong et al., "Synthesis and crystal structure of two novel nickel (imidazole) complexes having hydrogen-bonded networks" Journal of Molecular Structure, 740(1-3), 2005, 153-158.
Kronina et al., "Characterisation by immobilised metal ion affinity chromatographic procedures of the binding behaviour of several synthetic peptides designed to have high affinity for Cu(II) ions" Journal of Chromatography A, 852(1), 1999, 261-272.
Lee et al., "Ni/NiO Core/Shell Nanoparticles for Selective Binding and Magnetic Separation of Histidine-Tagged Proteins", Journal of the American Chemical Society, 128(33) 2006, 10658-10659.
Li et al., "An impedance immunosensor for the detection of the phytohormone abscisic acid", Analytical and Bioanalytical Chemistry, 391(8), 2008, 2869-2874.
Mammen et al., "Polyvalent Interactions in Biological Systems: Implications for Design and Use of Multivalent Ligands and Inhibitors", Angewandte Chemie-International Edition (37)20: 1998, 2754-2794.
Mulder et al, "Multivalency in supramolecular chemistry and nanofabrication", Organic & Biomolecular Chemistry, 2004, 2, 3409-3424.
Nam et al., "Bioactive Protein Nanoarrays on Nickel Oxide Surfaces Formed by Dip-Pen Nanolithography", Angewandte Chemie-International Edition, 43(10): 2004 1246-1249.
Quinones et al., "Functionalization of nickel oxide using alkylphosphonic acid self-assembled monolayers" Thin Solid Films 516 (2008) 8774-8781.
Shojaei et al., "Application of quartz crystal nanobalance and principal component analysis for the detection and determination of histidine". Analytical and Bioanalytical Chemistry 31:2875-2880, 2008.
Wang et al., "Electronic and vibrational properties of nickel sulfides from first principles", The Journal of Chemical Physics, 127, 214705, 2007, 8 pages.

* cited by examiner

OXIDATION STATE SENSORS AND METHODS FOR TRANSITION METAL ALLOYS

CROSS-REFERENCE TO RELATED APPLICATIONS

This application is a National Stage of International Application No. PCT/GB2010/000769, filed Apr. 16, 2010, which claims the benefit of GB 0907110.1, filed Apr. 24, 2009; all of the above-referenced applications are incorporated by reference in their entirety.

TECHNICAL FIELD OF THE INVENTION

The present invention relates to methods of treating an alloy surface to discriminate between oxidation states of transition metals in the alloy. The present invention is also concerned with the use of a sensor for discriminating between oxidation states of transition metals, and an alloy with an oxidation state sensor molecule associated with it.

BACKGROUND

Alloys are used in many components of the automotive, aeronautical and nautical industries. Alloys comprise at least one metallic element and at least one other element, metallic or non-metallic. Some properties of the alloy are typically enhanced over their individual component elements, such as increased tensile strength or thermal resistance.

In use, alloy components often experience high temperature and pressure conditions. These conditions lead to an increased rate of degradation of the components. Typically, degradation is caused by corrosion and oxidation. Degradation of the component weakens and reduces the desired properties of the alloys. Naturally, the surface of the components are often particularly susceptible to degradation.

The weakening of alloy components caused by degradation limits the lifetime of each component. Current methods for testing the degradation of alloy components are standard metallurgical methods, such as X-ray diffraction, electron microscopy and ion beam analysis. Obtaining a sample of the component to be used in such methods usually causes damage to the component, so that the component may not be used again. In some cases, the method itself may damage the section of the alloy that is being tested.

The lifetime of a component is estimated from average lifetime, calculated from analysis of previous components. The time that each component is used in service is significantly less than these average lifetimes, for safety reasons. This is particularly relevant in the aeronautical industry.

SUMMARY OF THE INVENTION

The present inventors have noted that there is a need for the lifetime of alloy components to be assessed more conveniently. The inventors have realised that it is desirable to have a method that can be used to determine the distribution of degradation in an alloy component, preferably without having to damage, dismantle or destroy the component.

The present inventors have found that discriminating between transition metals in one oxidation state and transition metals in another oxidation state may allow the distribution of degradation to be determined. This may also assist in establishing the extent of any such degradation.

Further, it is desirable for the method to be non-destructive, so that the components may be re-used after assessment of degradation. The present invention therefore relates to a method of applying a sensor molecule to an alloy surface to selectively associate with a transition metal in the surface layer of the alloy.

In a first aspect, the present invention provides a method of discriminating between, in a surface layer of an alloy comprising a transition metal, a first transition metal in a first oxidation state and a second transition metal in a second oxidation state different from the first oxidation state, the method comprising the step of:

(i) applying an oxidation state sensor molecule to the surface of the alloy, wherein the oxidation state sensor molecule is capable of selectively associating with the first transition metal, such that the distribution of the oxidation state sensor molecule on the surface can be used to discriminate between the first and second transition metals.

The alloy may form part of an industrial component e.g. a vehicle component, for example an aircraft component. Thus, the method is suitably a method of discriminating between first and second transition metals in an aircraft component. Suitably, the method is a method of determining degradation, especially the distribution of degradation, in an aircraft component. Nevertheless, the method can also be applied to other alloy-containing components, for example components of other types of vehicle (e.g. cars, boats, etc). Alloy aircraft components include, but should not be limited to, turbine blades, engine casings, aerofoils, nozzle guide vanes, fuel injectors, shrouds, heat shields and temperature resisting tiles, reheat systems and nozzles.

More generally, suitably the allow forms part of a component that is in use exposed to degradation conditions, e.g. oxidative conditions such as high temperatures.

Alloys typically comprise metallic elements of oxidation state zero. Degradation of the metallic elements leads to the presence of metals with an oxidation state greater than zero being present in the surface layer. The presence of these degradation product metals may weaken and reduce the structural properties of the alloy. When degradation becomes too great, an alloy component may not be used further in service.

Thus, application of an oxidation state sensor molecule (hereinafter: "sensor") to the surface of an alloy makes it possible to discriminate between a first transition metal in a first oxidation state and a second transition metal in a second oxidation state. The sensor is capable of selectively associating with a first transition metal of a first oxidation state. This suitably makes it possible for distribution of degradation in an alloy to be determined by the selective association of the sensor with a transition metal in one oxidation state over a transition metal of a different oxidation state.

Having obtained information regarding the distribution of degradation, an analysis of the lifetime of an alloy component may be carried out on an individual component basis. Thus, for example, if a component has degraded more than expected from the average lifetime estimations, the component may be taken out of service early. Equally, if a component has not degraded as much as expected from the average lifetime estimations, the component may stay in service for longer. As expected lifetime estimations are underestimated as a precaution, the method of the first aspect may be used to extend the service life of components.

The sensor may be applied to the surface of an alloy by any known deposition method, including dipping, spraying, brushing and painting. Preferably, the sensor is applied as a solution. Methods of applying a solution are well-known and are versatile. The application of a solution allows the sensor to be applied homogeneously to the surface. More preferably, the sensor is applied as an aqueous solution. Water is an inexpensive solvent that is readily available and has no impact on waste management or the environment.

The method has further advantages of being applicable to a large surface area. This allows the method to be used to analyse different areas of a component simultaneously. The method also benefits from not being restricted by complex alloy component shape or undulation. The sensor may be applied to any alloy surface regardless of its form. This is particularly relevant to aeronautical components.

The first oxidation state may be greater than the second oxidation state. Alternatively, the first oxidation state may be lower than the second oxidation state. If the first or second oxidation state is zero, the other oxidation state is non-zero, and, preferably, the other oxidation state is greater than zero. In other words, if the first oxidation state is zero, the second oxidation state is non-zero or greater than zero, and if the second oxidation state is zero, the first oxidation state is non-zero or greater than zero.

In a preferred embodiment, the first oxidation state is an oxidation state greater than zero and the second oxidation state is zero. Thus, the first transition metal may be the product of degradation of the alloy, for example an oxide formed by exposure to high temperatures. In such embodiments, the sensor is capable of selectively associating with the degradation product of the alloy, and thus the method allows for discrimination between the degradation product of the alloy and the alloy.

Alternatively, the first transition metal in the first oxidation state may be in an oxidation state of zero and the second transition metal in the second oxidation state may be in an oxidation state greater than zero. This method may also be used to discriminate between degradation products of the alloy and the alloy. In this embodiment, the sensor selectively associates with the metallic element transition metals in the surface.

The first and second transition metals may be different transition metal elements, for example Ni and Co. Alternatively, in a preferred embodiment, the first and second transition metals are the same transition metal element, for example both Ni. In such embodiments, the first and second transition metals differ only in their oxidation state.

Preferably the alloy is a transition metal alloy. More preferably, the transition metal alloy comprises Ni and optionally Co or Cr. Common transition metal alloys include, but are not limited to, those of Ni, such as inconel, German silver, Hastelloy® and nicrosil, those of cobalt, such as Megallium®, Stellite® and Vitallium®, those of copper, such as brass, bronze and cupro-nickel, and those of iron, such as steel, stainless steel and silicon steel.

Preferably, the alloy comprises more than two transition metals. For example, the alloy may comprise a third transition metal in a third oxidation state. The alloy may further comprise a fourth transition metal in a fourth oxidation state. Each transition metal need only differ from the other transition metals by either its transition metal element, e.g. Ni and Co, or its oxidation state. In other words, there may be any permutation of transition metal elements in oxidation states.

Preferably, the first and second transition metals are first row transition metals. First row transition metals are commonly used in alloys, and, when in an oxidation state greater than zero, are more electron deficient than second or third row transition metals.

The alloy may be a single crystal metal alloy. Grain boundaries may interfere with creep and so it is particularly advantageous if the alloy of the present invention is a single crystal metal superalloy. Single crystal metal alloys are typically used for aircraft components, such as turbine blades, which are subjected to severe environmental exposure. Single crystal turbine blade alloys are subjected to very high temperature conditions, which form an oxidising environment.

The alloy may be polycrystalline. The method of the first aspect may be used to determine crystal grain boundaries. In particular, greater degradation might be expected to occur at a grain boundary, and therefore transition metals in an oxidation state greater than zero may be present at a higher concentration as compared to other parts of the alloy.

A class of alloys of particular interest are superalloys. Superalloys are alloys that display excellent mechanical strength and creep resistance at high temperatures. These properties make them ideal for use in aircraft components, such as turbine blades, aerofoils and engine casings. Under the high temperature and pressure conditions experienced by these components, degradation of the metallic elements occurs in the superalloy. As in the general class of alloys, the product of degradation is typically metals of an oxidation state greater than zero. The method of the first aspect may provide a way of determining the extent and location of degradation in a superalloy.

The superalloy may be solid solution strengthened or precipitation hardened, and may be cast alloys or PHIP alloys. Superalloys include but should not be limited to: HAYNES® 188, HAYNES® 230, HASTELLOY® X, IN-738LC, MAR-M247LC, CM247LC, Inconels, alloy 718, PK33, Udimet®720LI, RR1000, PE16, Waspaloy, René alloys (e.g. René 41, René 80, René 95), Haynes alloys, MP98T, TMS alloys, and CMSX series and RR3000 single crystal alloys, Mar-M-002, C1023, PE11, PE16, IN713, RS5, EP741 NP (Russian alloy), N18-Snecma® alloy, LC Astroloy, René 88DT-GEAE alloy, Udimet® 720, AF115, AF2-1 DA-6, PA101 and MERL 76. Further discussion of superalloys and further examples may be found in "The Superalloys, Fundamentals and Applications" by Roger C. Reed, Cambridge University Press, 2006, ISBN-13 978-0-521-85904-2, which is incorporated herein for reference.

Preferably the superalloy comprises Ni. More preferably the superalloy comprises Ni and Cr. The superalloy may be selected from the group of MAR-M-002, CMSX®4, SRR99, C1023 and $Ni_{12}Cr_{10}CO_2Mo_4W_{3.5}Al_4Ti_4Ta_{0.01}B_{0.09}Zr_{0.1}C_{0.5}Hf$.

For convenience, the following discussion refers to embodiments wherein the first oxidation state is greater than zero and the second oxidation state is zero. However, the optional and preferred features discussed below also apply in the alternative arrangement wherein the first oxidation state is zero and the second oxidation state is greater than zero.

Preferably, the first transition metal is selected from the group consisting of: Ni(II), Ni(III), Co(II), Co(III), Fe(II), Fe(III), Fe(V), Cu(I), Cu(II), Mn(II), Mn(III), Mn(IV), Mn(V), Mn(VI), Mn(VII), Cr(II), Cr(III), Cr(VI), V(II), V(III), V(IV), V(V), Ti(II), Ti(III), Ti(IV) and Sc(II).

The oxidations states shown are electron deficient forms of the preferred first row transition metals. The electron-rich sensor may strongly associate with a first transition metal of the type described above. Discrimination between first transition metals of this sort and a second transition metal in an oxidation state of zero may be particularly effective.

More preferably, the first transition metal is selected from the group consisting of: Ni(II), Ni(III), Co(II), Co(III), Fe(II), Fe(III), Fe(V), Cu(I) and Cu(II).

More preferably, the first transition metal is selected from the group consisting of: Ni(II), Ni(III), Co(II) and Co(III). Most preferably, the first transition metal is Ni(II) or Ni(III).

The second transition metal is preferably be a first row transition metal. Preferably, the second transition metal is selected from the group consisting of: Ni(0), Co(0), Fe(0), Cu(0), Mn(0), Cr(0), V(O), Ti(0) and Sc(0).

More preferably, the second transition metal is selected from the group consisting of: Ni(0), Co(0), Fe(0) and Cu(0). More preferably, the second transition metal is Ni(0) or Co(0). Most preferably, the second transition metal is Ni(0).

Preferably, the sensor has a oxidation state discriminating group. When the first transition metal is in an oxidation state greater than zero, the oxidation state discriminating group is, preferably, an electron-rich group. Suitably, such electron-rich groups may selectively associate with transitional metals in an oxidation state greater than zero, and are therefore capable of discriminating between a first transition metal in an oxidation state greater than zero and a second transition metal in an oxidation state of zero.

More preferably, the sensor comprises a Lewis base group. Suitably, the sensor is a Lewis base. In embodiments, the Lewis base group selectively associates with the first transition metal in an oxidation state greater than zero in the surface layer of the alloy.

The interaction between the sensor and the alloy surface may be a reversible interaction. This allows the sensor to be reversibly associated with the alloy surface. This enables the method of the first aspect to provide a non-destructive technique, so that an alloy component may be re-used after the method has been employed.

The interaction between the sensor and the alloy surface may be a non-covalent interaction. The interaction may be a coordination interaction between the transition metal and the sensor. The sensor may act as a ligand to the transition metal.

Any Lewis base group is suitable for use as a sensor. For example the any Lewis base group may bind an electron-deficient transition metal, i.e. a transition metal in an oxidation state greater than zero.

Preferably, the sensor includes an atom with an accessible lone pair. A sensor with an atom with an accessible lone pair may form part of a Lewis base group. The lone pair may increase the affinity of the sensor to the electron-deficient transition metal in an oxidation state greater than zero. Preferably, the Lewis base group includes an electron-rich atom which is selected from the group consisting of N, O and S.

Preferably, the sensor comprises an aromatic or aliphatic heterocyclic group. Suitable examples of the heterocyclic group include, but are not limited to pyrrole, furan, thiophene, pyrazole, imidazole, oxazole, isoxazole, thiazole, isothiazole, triazole, thiatriazole, pyridine, pyran, thiapyrane, piperizine, oxazine, thiazine, and their derivatives.

More preferably, the sensor comprises a heteroaromatic group. Heteroaromatic are more electron-rich than aliphatic groups and so increase the affinity of the sensor to the first transition metal in an oxidation state greater than zero. Suitable examples of the heterocyclic group include, but are not limited to pyrrole, imidazole, pyrazole, oxazole, thiaozle, pyridine, pyridazine, pyrimidine and pyrazine and their derivatives.

More preferably, the sensor comprises an imidazole or imidazolium unit. The present inventors have found that imidazole groups have a particular affinity for Ni(II) over Ni(0) in alloy surfaces. Imidazole groups are suitable for use in a sensor to discriminate between transition metals in different oxidation states in a surface layer of an alloy.

The sensor and any of its optional groups may be optionally substituted. Optional substituents include, but should not be limited to: halo; hydroxy; ether (e.g., $C_{1-7}$alkoxy); formyl; acyl (e.g., $C_{1-7}$alkylacyl, $C_{5-20}$arylacyl); acylhalide; carboxy; ester; acyloxy; amido; acylamido; thioamido; tetrazolyl; amino; nitro; nitroso; azido; cyano; isocyano; cyanato; isocyanato; thiocyano; isothiocyano; sulfhydryl; thioether (e.g., $C_{1-7}$alkylthio); sulfonic acid; sulfonate; sulfone; sulfonyloxy; sulfinyloxy; sulfamino; sulfonamino; sulfinamino; sulfamyl; sulfonamido; $C_{1-7}$alkyl (including, e.g., unsubstituted $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; or $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl)).

Preferably, the sensor includes an α-amino acid. α-Amino acids possess electron-rich N and O Lewis basic groups. Furthermore, they are readily available and their chemistry is well understood. Many α-amino acids also include an electron-rich atom in the α-amino acid side chain i.e. in R if the α-amino acid is represented by the formula: $H_2NCH(R)COOH$. These are of particular interest and include, but are not limited to lysine, histidine, methionine, threonine, tryptophan, asparagine, aspartic acid, glutamate, glutamine, serine, tyrosine, arginine and cysteine, and their derivatives.

More preferably, the sensor contains a histidine moiety. Histidine contains an imidazole group in the α-amino acid side chain. Imidizole groups, as described herein, have an affinity for electron deficient transition metals, and in particular for Ni(II).

Preferably, the sensor comprises a plurality of oxidation state discriminating groups. By increasing the number of oxidation state discriminating groups, the sensor may benefit from cooperative binding to the alloy surface. Cooperative binding is an effect associated with coordinating molecules that have more than one binding group. The binding potential of a second and subsequent binding groups is usually reduced when a first binding group is associated with the species to be bound.

More preferably, the sensor comprises an oligomer or polymer, wherein the repeating units comprise oxidation state discriminating groups. Preferably the sensor is a polymer of the Lewis base.

Polymers may be more easily isolated and purified as compared to monomer analogues. A polymer sensor may also cooperatively bind to the surface. A further advantage of a polymer sensor is that it may be possible to tailor the size of the sensor to particular features on the surface. For example, it may be possible to adapt the size of the sensor (e.g. by varying the number of repeating units) to the size of a surface feature.

Preferably, the sensor comprises a polymer with repeating units that include an imidazole group, for example poly(histidine). Preferably, the sensor comprises a polymer of imidazole repeating units, in other words, poly(imidazole).

More preferably, the sensor comprises a polymer of α-amino acid oxidation state discriminating groups. α-amino acids are easily polymerised to form peptide linkages. In a more preferred embodiment, the sensor comprises poly(histidine). Poly(histidine) contains repeating units that include an imidazole group. The present inventors have shown that these sensors may selectively associate with transition metals in an oxidation state greater than zero.

The polymer sensor may have any number of repeating units. Preferably, the polymer sensor has 100 or fewer repeating units. Preferably, the polymer sensor comprises between 5 and 50 repeating units. More preferably, the polymer sensor comprises between 15 and 40 repeating units. Most preferably, the polymer sensor comprises between 20 and 30 repeating units.

Preferably, the sensor further includes; is attached to; is integral with; is bonded to; or is conjugated with a probe group. The skilled reader will recognise that there are many probe groups that may be used to produce a signal to be detected. For example, the probe may be a luminescent or radio-active group. The inclusion of a probe group into the sensor facilitates the investigation of the distribution of the first transition metal by providing a detectable signal from the sensor.

Preferably the probe group is a luminescent group. An advantage of luminescent materials is that they are easily handled and, in contrast to radioactive materials, their radiation, generally, does not cause harm to humans.

Luminescent groups may be photoluminescent, chemoluminescent or electroluminescent. Preferably, the probe group is photoluminescent. Photoluminescent groups may be fluorescent or phosphorescent.

Preferably, the probe group is fluorescent or a fluorophore. Fluorescence is well understood and there are many fluorophores known in the art. Such fluorophores include, but should not be limited to, fluorescein, fluorescein isothiocyanate (FITC), any member of the rhodamine series, coumarin, cyanine, calcein, oregon green, leucophor, dansyl, phorwhite, any member of the Alexa Fluor® series and any member of the SYTO® series.

Other fluorophores that may be used may be found in Haugland, R. 1996. Handbook of Fluorescent Probes and Research Chemicals, 6th ed. Molecular Probes, Inc., and Eugene, Oreg. & Herman, B. 1998 Fluorescence Microscopy. Bios Scientific Publishing, Oxford, England, both of which are incorporated herein.

Preferably the fluorophore is fluorescein or a fluorescein derivative. Fluorescein is a widely used fluorophore that emits in the yellow range of the visible spectrum.

An amine group in a poly-histidine may be reacted with fluorescein isothiocyanate to form a poly-histidine-fluorescein conjugate. The conjugate may be formed before the sensor is applied to the alloy surface. The conjugate may be formed on the alloy surface after the sensor has been applied to the surface.

Preferably, the method of the first aspect may further include the step of:
(ii) removing excess oxidation state sensor molecule from the surface of the alloy.

Preferably, more than 50% of the excess sensor is removed from the surface of the alloy. Preferably, substantially all excess sensor is removed from the surface of the alloy. More preferably, all excess sensor is removed from the surface of the alloy. Removing excess sensor that has not coordinated to the surface is advantageous to ensure that the sensor is associated with and located in the area of the first transition metal in the first oxidation state.

Preferably, excess sensor is washed from the surface. More preferably, the surface is washed in step (ii) with a solvent or buffered solution. More preferably, water is used as the solvent or the buffered solution is an aqueous solution.

Preferably, the method includes the step of:
(iii) modifying the oxidation state sensor molecule on the surface of the alloy.

Modification of the sensor on the surface of the alloy may include reacting the sensor on the surface with a chemical to produce a detectable change in the surface characteristics. Preferably, the modification includes washing the surface with a solution of a probe group as described above to incorporate the probe group into the sensor.

Preferably, the method includes the step of:
(iv) detecting a signal from the sensor on the surface of the alloy.

By detecting the sensor, the method allows the identification of areas comprising the first transition metal. Where the first transition metal is in an oxidation state greater than zero, the detection of the location of the first transition metal yields information about the extent and location of degradation of the alloy. Preferably, the signal of the sensor is detected in step (iv) by imaging. Such a step can be carried out using an imaging device. Many imaging devices are known in the art and include, but are not limited to a camera or microscope.

The imaging means may include multiple camera systems or variable focus microscopes. Images from such systems may be analysed by a computer and converted into composite confocal images. Such images can be associated with spatial positioning data to create a (virtual) three dimensional topographic image. The lighting may be tuned for contrast and response of, for example, the fluorophore. The cameras and component may be manipulated together or independently. Fibre-optic probes and mirror based systems may be used to investigate cavities.

In a preferred embodiment, the method includes the step of:
(v) removing oxidation state sensor molecules from the alloy surface.

Preferably, more than 50% of the coordinated sensor is removed from the surface of the alloy. Preferably, substantially all the coordinated sensor is removed from the surface of the alloy. More preferably, all coordinated sensor is removed from the surface of the alloy.

The benefit of removing the sensor is that the alloy component may be used again or subjected to subsequent analysis. Preferably, the sensor is removed with an aqueous acid solution. The acid solution effectively removes the coordinated sensor without damaging the alloy. More preferably, the sensor is removed with an aqueous acetic acid solution. Acetic acid is effective, inexpensive and readily available.

If step (iv) is also present in the method, step (v) may be performed at any time after the signal of the coordinated sensor has been detected.

In the first aspect of the invention any one or more of steps (ii)-(v) may be optionally included and are not dependent on each other in order to be performed.

Thus, a preferred embodiment of the first aspect of the invention is a method of discriminating between, in a surface layer of an alloy comprising a transition metal, a first transition metal in a first oxidation state and a second transition metal in a second oxidation state different from the first oxidation state, the method comprising the steps of:
(i) applying an oxidation state sensor molecule to the surface of the alloy; and
(ii) detecting the oxidation state sensor molecule on the surface of the alloy, wherein the oxidation state sensor molecule is capable of selectively associating with the first transition metal, such that the distribution of the oxidation state sensor molecule on the surface can be used to discriminate between the first and second transition metals.

A more preferred embodiment of the first aspect of the invention is a method of discriminating between, in a surface layer of an alloy comprising a transition metal, a first transition metal in a first oxidation state and a second transition metal in a second oxidation state different from the first oxidation state, the method comprising the steps of:
(i) applying an oxidation state sensor molecule to the surface of the alloy and washing excess oxidation state sensor molecule from the surface; and
(ii) detecting the oxidation state sensor molecule on the surface of the alloy, wherein the oxidation state sensor molecule comprises a Lewis base group capable of selectively associating with the first transition metal, and a probe group for emitting a detectable signal, such that the distribution of the oxidation state sensor molecule on the surface can be used to discriminate between the first and second transition metals.

If the sensor includes a probe group either as applied, attached or part of the sensor or through modification of the sensor on the surface to form a probe group, the sensor may be detected by a signal emitted from the probe group.

In a second aspect, the present invention provides a method of discriminating between, in a surface layer of an alloy comprising a transition metal, a first transition metal in a first oxidation state and a second transition metal of a second oxidation state different from the first oxidation state, wherein an oxidation state sensor molecule is selectively associated with the first transition metal, the method comprising the step of:
(i) modifying the oxidation state sensor molecule on the surface of the alloy, such that the distribution of the modified oxidation state sensor molecule on the surface can be used to discriminate between the first and second transition metals.

The method of the second aspect allows an sensor to be modified to discriminate between the first and second transition metals. Such modification may be to react the sensor with a reactive probe so that the sensor includes a probe group. The probe group may be any group as defined above.

An alternative method of the second aspect is to modify the sensor so that a physical characteristic of the sensor is identifiably changed. The method may include reacting the sensor to increase the sensor's hydrophobicity. For example, the sensor may be reacted with a fatty acid group to increase the hydrophobicity of the sensor.

In a third aspect, the present invention provides a method of discriminating between, in a surface layer of an alloy comprising a transition metal, a first transition metal in a first oxidation state and a second transition metal of a second oxidation state different from the first oxidation state, wherein an oxidation state sensor molecule is selectively associated with the first transition metal, the method comprising the step of:
(i) detecting the oxidation state sensor molecule on the surface of the alloy, such that the distribution of the oxidation state sensor molecule is detected and can be used to discriminate between the first and second transition metals.

The method of the third aspect allows the distribution of any sensor that is associated with the first transition metal to be determined. This allows the location of any degradation of the alloy to be determined. It may also be used to determine the extent of degradation.

In a fourth aspect, the present invention provides a method for discriminating between, in a surface layer of an alloy comprising a transition metal, a first transition metal in a first oxidation state, a second transition metal in a second oxidation state different from the first oxidation state and a third transition metal in a third oxidation state different from the first and second oxidation states, the method comprising the steps of:
(i) applying a first oxidation state sensor molecule to a first portion of the surface of the alloy,
wherein the first oxidation state sensor molecule is capable of selectively associating with the first transition metal, such the distribution of the first oxidation state sensor molecule can be used to discriminate between the first and second transition metals; and
(ii) applying a second oxidation state sensor molecule to a second portion of the surface of the alloy,
wherein the second oxidation state sensor molecule is capable of selectively associating with the third transition metal, such the distribution of the second oxidation state sensor molecule can be used to discriminate between the first, second and third transition metals.

The method of the fourth aspect provides that more than one sensor may be applied to discriminate between first, second and third transition metals in a surface layer of an alloy. The benefit of applying a first and second sensor is that one can discriminate more than one transition metal in an alloy surface layer.

The first and second portion may be the same portion of the surface.

In a fifth aspect, the present invention provides a use of an oxidation state sensor molecule as described herein for discriminating between, in a surface layer of an alloy comprising a transition metal, a first transition metal in a first oxidation state and a second transition metal in a second oxidation state different from the first oxidation state.

In a sixth aspect, the present invention provides an alloy body having a surface comprising a transition metal and an oxidation state sensor molecule associated with the surface, the oxidation state sensor molecule being capable of discriminating between a first transition metal in a first oxidation state and a second transition metal in a second oxidation state different from the first oxidation state by selectively associating with the first transition metal.

Preferably, the alloy body further includes a coating to coat part of the alloy body. More preferably, the coating comprises a single metal or an alloy. At least part of the alloy body surface is exposed, such that the sensor may be detected.

In a seventh aspect, the present invention provides a composition adapted for the application to the surface of an alloy comprising a transition metal, the composition including:
(i) an oxidation state sensor molecule as defined in any of the above aspects; and
(ii) a buffer.

In a preferred embodiment of the above aspects, the present invention provides a method of discriminating between, in a surface layer of an alloy aircraft component comprising a transition metal, a first transition metal in an oxidation state greater than zero and a second transition metal in an oxidation state of zero, the method comprising the steps of:
(i) applying an oxidation state sensor molecule to the surface of the alloy;
(ii) removing excess sensor from the surface;
(iii) detecting the sensor; and
(iv) removing coordinated sensor from the surface of the alloy;
wherein the sensor comprises a probe group and the sensor is capable of selectively associating with the first transition metal, such that the distribution of the oxidation state sensor molecule on the surface can be used to discriminate between the first and second transition metals.

The aircraft component may be a turbine blade, an engine casing, an aerofoil, a nozzle guide vane, a fuel injector, a shroud, a heat shield, a temperature resisting tile, a reheat system or a nozzle. Preferably, the aircraft component is selected from the group consisting of: a turbine blade, an engine casing and an aerofoil.

Any one of the aspects of the present invention may be combined with any one or more of the other aspects. Furthermore, any of the optional or preferred features of any one of the aspects may apply to any of the other aspects. In particular, the definitions of the oxidation state sensor molecule, first transition metal, second transition metal and probe group of the first aspect may apply to all other aspects of the invention.

In particular, optional features associated with a method or use may apply to a product, and vice versa.

DESCRIPTION OF THE DRAWINGS

FIG. 1: Side view of a nickel superalloy rod RR73844 imaged; 1A: after the sensor has been applied to the surface; and 1B: after the rods have been washed with acetic acid to remove the sensor.

FIG. 2: Side view of nickel superalloy rods CMSX-4, SRR99 and C1023 imaged; 2A: after the sensor has been applied to the surface; and 2B: after the rods have been washed with acetic acid to remove the sensor.

FIG. 3: Side view of a nickel superalloy turbine blade imaged; 3A: after the sensor has been applied to the surface; and 3B: after the rods have been washed with acetic acid to remove the sensor.

DEFINITIONS

Lewis Base Group

A Lewis base group is an atomic or molecular species that may donate electrons to an electron-deficient moiety, e.g. a Lewis acid. Lewis base groups typically have an accessible lone pair of electrons. These lone pairs are often in the HOMO. Examples of Lewis base groups include compounds of N, P, As, Sb and Bi in oxidation state 3, compounds of O, S, Se and Te in oxidation state 2, including water, ethers, ketones and sulphoxides and molecules such as carbon monoxide.

Ligand

A ligand is an atom, ion or molecule that may bond to a central metal. The interaction between a metal and a ligand typically involves the donation of one or more electrons from the ligand to the metal.

Alloy

Alloys comprise at least one metallic element, and may further comprise one or more metallic or non-metallic elements. Alloys usually have different properties from those of the component elements.

Alloying one metal with other metal(s) or non metal(s) often enhances its properties. Engineering properties, such as tensile strength and shear strength may be substantially different from those of the constituent materials.

Superalloy

A superalloy, or high-performance alloy, is an alloy that exhibits excellent mechanical strength and creep resistance at high temperatures, good surface stability, and corrosion and oxidation resistance.

Examples of superalloys include Ni-based superalloys such as MAR-M-002, which is a cast nickel based super alloy with a nominal chemical composition: 10.1 Co, 9.9 W, 8.9 Cr, 5.8 Al, 2.5 Ta, 1.5 Ti, 1.5 Hf, 0.1 Mo, 0.03 Zr, 0.13 C, balance Ni.

Further examples of Ni-based superalloys include:
CMSX4: nominal composition: 9.6 Co, 6.5 Cr, 6.5 Ta, 6.4 W, balance Ni;
SRR99: nominal composition: 9.5 W, 8.5 Cr, 5.5 Al, 5.0 Co, 2.8 Ta, balance Ni; and
C1023: nominal composition: 15.5 Cr, 9.7 Co, 8.3 Mo, 4.1 Al, balance Ni.

Other examples of Ni-based superalloys include René 95, René 88 DT, Astroloy, MERL 76, IN-100, N-18 and EP741 NP. Their compositions, given by element as % by weight, are given in Table I.

TABLE I compositions of superalloys.

| Element | René 95 | René 88 DT | As-troloy | MERL 76 | IN-100 | N-18 | EP741NP |
|---|---|---|---|---|---|---|---|
| C | 0.06 | 0.03 | 0.02 | 0.02 | 0.07 | 0.02 | 0.04 |
| Cr | 13 | 16 | 14.5 | 12.4 | 12.5 | 11.5 | 9.0 |
| Co | 7 | 13 | 16.5 | 18.5 | 18.5 | 15.7 | 15.75 |
| Mo | 3.5 | 4.0 | 5.0 | 3.2 | 3.2 | 6.5 | 3.85 |
| W | 3.5 | 4.0 | — | — | — | — | 5.55 |
| Ti | 2.5 | 3.7 | 3.5 | 5.0 | 4.4 | 4.35 | 1.8 |
| Al | 3.5 | 2.0 | 4.0 | 4.3 | 5.0 | 4.35 | 5.35 |
| B | 0.007 | 0.015 | 0.03 | 0.02 | 0.02 | 0.02 | 0.015 |
| Zr | 0.005 | 0.03 | 0.06 | 0.05 | 0.06 | 0.03 | — |
| Nb | 3.5 | 0.7 | — | 1.65 | — | — | 2.6 |
| Ni | Bal. | Bal. | Bal. | Bal. | Bal. | Bal. | Bal. |
| Other | — | — | — | — | V 0.8 | Hf 0.5 | V 0.015 |

Bal. represents to Balance.

Heterocyclic:

Examples of heterocyclic groups (some of which are also heteroaryl groups) which comprise fused rings, include, but are not limited to:

$C_9$ heterocyclic groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ heterocyclic groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ heterocyclic groups (with 2 fused rings) derived from benzodiazepine ($N_2$);

$C_{13}$ heterocyclic groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and $C_{14}$ heterocyclic groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methylpyrrole. Examples of N-substitutents include, but are not limited to $C_{1-7}$alkyl, $C_{3-20}$heterocyclyl, $C_{5-20}$aryl, and acyl groups.

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{5-20}$heterocyclyl, $C_{3-15}$heterocyclyl, $C_{5-15}$heterocyclyl, $C_{3-12}$heterocyclyl, $C_{5-12}$heterocyclyl, $C_{3-10}$heterocyclyl, $C_{5-10}$heterocyclyl, $C_{3-7}$heterocyclyl, $C_{5-7}$heterocyclyl, and $C_{5-6}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Heteroaromatic:

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and,

$N_4$: tetrazole ($C_5$).

Amino Acids

The term "α-amino acid," as used herein, pertains to compounds of the following formula:

The term "α-amino acid side chain," as used herein, pertains to the group, R, in the following formula for an α-amino acid:

α-Amino Acid Group: The term "α-amino acid group," as used herein, pertains to a group:

which corresponds to an α-amino acid of the following formula:

Examples of α-amino acids include both natural amino acids and non-natural amino acids. The natural amino acids include: those with nonpolar (hydrophobic) R groups: alanine, Ala, A; isoleucine, Ile, I; leucine, Leu, L; methionine, Met, M; phenylalanine, Phe, F; proline, Pro, P; tryptophan, Trp, W; and valine, Val, V; those with polar but uncharged R groups: asparagine, Asn, N; cysteine, Cys, C; glutamine, Gln, Q; glycine, Gly, G; serine, Ser, S; threonine, Thr, T; and tyrosine, Tyr, Y; those with (potentially) positively charged R groups: arginine, Arg, R; histidine, His, H; and lysine, Lys, K; and those with (potentially) negatively charged R groups: aspartic acid, Asp, D; glutamic acid, Glu, E.

Examples of modified natural amino acids include, but are not limited to, hydroxyproline, γ-carboxyglutamate, and O-phosphoserine.

Examples of non-natural α-amino acids include: β-(napth-2-yl)alanine, β-(2-cyanophenyl)alanine, β-(ethinyl)alanine, β-(furan-2-yl)alanine, α-(thien-2-yl)alanine, β-(4-pyridinyl) alanine, Substituents The phrase "optionally substituted," as used herein, pertains to a parent group which may be unsubstituted or which may be substituted.

Unless otherwise specified, the term "substituted," as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl. Note that the first prefix may vary according to other limitations; for example, for unsaturated alkyl groups, the first prefix must be at least 2; for cyclic and branched alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH═CH$_2$), 1-propenyl (—CH═CH—CH$_3$), 2-propenyl (allyl, —CH—CH═CH$_2$), isopropenyl (1-methylvinyl, —C(CH$_3$)═CH$_2$), butenyl ($C_4$), pentenyl ($C_5$), and hexenyl ($C_6$).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, —C≡CH) and 2-propynyl (propargyl, —CH$_2$—C≡CH).

Cycloalkyl: The term "cycloalkyl," as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g., partially unsaturated, fully unsaturated), which moiety has from 3 to 20 carbon atoms (unless otherwise specified), including from 3 to 20 ring atoms. Thus, the term "cycloalkyl" includes the sub-classes cycloalkyenyl and cycloalkynyl. Preferably, each ring has from 3 to 7 ring atoms. Examples of groups of cycloalkyl groups include $C_{3-20}$cycloalkyl, $C_{3-15}$cycloalkyl, $C_{3-10}$cycloalkyl, $C_{3-7}$cycloalkyl.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane (CO;

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds:
thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

unsaturated polycyclic hydrocarbon compounds:
camphene ($C_{10}$), limonene ($C_{10}$), pinene (CO;

polycyclic hydrocarbon compounds having an aromatic ring:
indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Alkylidene: The term "alkylidene," as used herein, pertains to a divalent monodentate moiety obtained by removing two hydrogen atoms from an aliphatic or alicyclic carbon atom of a hydrocarbon compound having from 1 to 20 carbon atoms (unless otherwise specified). Examples of groups of alkylidene groups include $C_{1-20}$alkylidene, $C_{1-7}$alkylidene, $C_{1-4}$alkylidene.

Examples of alkylidene groups include, but are not limited to, methylidene (═CH$_2$), ethylidene (═CH—CH$_3$), vinylidene (═C═CH$_2$), isopropylidene (═C(CH$_3$)$_2$), cyclopentylidene, and benzylidene (═CH-Ph).

Alkylidyne: The term "alkylidyne," as used herein, pertains to a trivalent monodentate moiety obtained by removing three hydrogen atoms from an aliphatic or alicyclic carbon atom of a hydrocarbon compound having from 1 to 20 carbon atoms (unless otherwise specified). Examples of groups of alkylidyne groups include $C_{1-20}$alkylidyne, $C_{1-7}$alkylidyne, $C_{1-4}$alkylidyne.

Examples of alkylidyne groups include, but are not limited to, methylidyne (ECH), ethylidyne (EC-CH$_3$), and benzylidyne (EC-Ph).

Carbocyclyl: The term "carbocyclyl," as used herein, pertains to a monovalent moiety obtained by removing a hydrogen atom from a ring atom of a carbocyclic compound, which moiety has from 3 to 20 ring atoms (unless otherwise specified). Preferably, each ring has from 3 to 7 ring atoms.

In this context, the prefixes (e.g., $C_{3-20}$, $C_{3-7}$, $C_{5-6}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$carbocyclyl, $C_{5-10}$carbocyclyl, $C_{3-7}$carbocyclyl, and $C_{5-7}$carbocyclyl.

Examples of carbocyclic groups include, but are not limited to, those described above as cycloalkyl groups; and those described below as carboaryl groups.

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{5-20}$heterocyclyl, $C_{3-15}$heterocyclyl, $C_{5-15}$heterocyclyl, $C_{3-12}$heterocyclyl, $C_{5-12}$heterocyclyl, $C_{3-10}$heterocyclyl, $C_{5-10}$heterocyclyl, $C_{3-7}$heterocyclyl, $C_{5-7}$heterocyclyl, and $C_{5-6}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{3-20}$aryl, $C_{5-20}$aryl, $C_{5-15}$aryl, $C_{5-12}$aryl, $C_{5-10}$aryl, $C_{5-7}$aryl, $C_{5-6}$aryl, $C_5$aryl, and $C_6$aryl.

The ring atoms may be all carbon atoms, as in "carboaryl groups." Examples of carboaryl groups include $C_{3-20}$carboaryl, $C_{5-20}$carboaryl, $C_{5-15}$carboaryl, $C_{5-12}$carboaryl, $C_{5-10}$carboaryl, $C_{5-7}$carboaryl, $C_{5-6}$carboaryl, $C_5$carboaryl, and $C_6$carboaryl.

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups." Examples of heteroaryl groups include $C_{3-20}$heteroaryl, $C_{5-20}$heteroaryl, $C_{5-15}$heteroaryl, $C_{5-12}$heteroaryl, $C_{5-10}$heteroaryl, $C_{5-7}$heteroaryl, $C_{5-6}$heteroaryl, $C_5$heteroaryl, and $C_6$heteroaryl.

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heterocyclic groups (some of which are also heteroaryl groups) which comprise fused rings, include, but are not limited to:

$C_9$heterocyclic groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$heterocyclic groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$heterocyclic groups (with 2 fused rings) derived from benzodiazepine ($N_2$);

$C_{13}$heterocyclic groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$heterocyclic groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methylpyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)= (also denoted —N$^+$ (→O$^-$)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms.

Monocyclic examples of such groups include, but are not limited to, those derived from:

$C_5$: cyclopentanone, cyclopentenone, cyclopentadienone;

$C_6$: cyclohexanone, cyclohexenone, cyclohexadienone;

$O_1$: furanone ($C_5$), pyrone ($C_6$);

$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:
$C_9$: indenedione;
$C_{10}$: tetralone, decalone;
$C_{14}$: anthrone, phenanthrone;
$N_1$: oxindole ($C_s$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$); benzodiazepinone ($C_{11}$); benzodiazepinedione ($C_{11}$);
$N_4$: purinone ($C_9$) (e.g., guanine).

Still more examples of cyclic groups which bear one or more oxo (=O) groups on ring carbon atoms include, but are not limited to, those derived from:
cyclic anhydrides (—C(=O)—O—C(=O)— in a ring), including but not limited to maleic anhydride ($C_5$), succinic anhydride ($C_5$), and glutaric anhydride ($C_6$);
cyclic carbonates (—O—C(=O)—O— in a ring), such as ethylene carbonate ($C_5$) and 1,2-propylene carbonate ($C_5$);
imides (—C(=O)—NR—C(=O)— in a ring), including but not limited to, succinimide ($C_5$), maleimide ($C_5$), phthalimide, and glutarimide ($C_6$);
lactones (cyclic esters, —O—C(=O)— in a ring), including, but not limited to, β-propiolactone, γ-butyrolactone, δ-valerolactone (2-piperidone), and ε-caprolactone;
lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);
cyclic carbamates (—O—C(=O)—NR— in a ring), such as 2-oxazolidone ($C_5$); cyclic ureas (—NR—C(=O)—NR— in a ring), such as 2-imidazolidone ($C_5$) and pyrimidine-2,4-dione (e.g., thymine, uracil) ($C_6$).

The above groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound or group as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

Alkoxy: —OR, wherein R is an alkyl group, for example, a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH($OR^1$)($OR^2$), wherein $R^1$ and $R^2$ are independently acetal substituents, for example, a $C_{1-7}$alkyl group, a $C_{3-20}$heterocyclyl group, or a $C_{5-20}$aryl group, preferably a $C_{1-7}$alkyl group, or, in the case of a "cyclic" acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)($OR^1$), wherein $R^1$ is a hemiacetal substituent, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —CH(OH)(OMe) and —CH(OH)(OEt).

Ketal: —CR($OR^1$)($OR^2$), where $R^1$ and $R^2$ are as defined for acetals, and R is a ketal substituent other than hydrogen, for example, a $C_{1-7}$alkyl group, a $C_{3-20}$heterocyclyl group, or a $C_{5-20}$aryl group, preferably a $C_{1-7}$alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)($OR^1$), where $R^1$ is as defined for hemiacetals, and R is a hemiketal substituent other than hydrogen, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR¹R², wherein R¹ and R² are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a $C_{1-7}$alkyl group, or, in the case of a "cyclic" amino group, R¹ and R², taken together with the nitrogen atom to which they are attached, form a heterocyclic ring having from 4 to 8 ring atoms. Amino groups may be primary (—NH₂), secondary (—NHR¹), or tertiary (—NHR¹R²), and in cationic form, may be quaternary (—⁺NR¹R²R³). Examples of amino groups include, but are not limited to, —NH₂, —NHCH₃, —NHC(CH₃)₂, —N(CH₃)₂, —N(CH₂CH₃)₂, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR¹R², wherein R¹ and R² are independently amino substituents, as defined for amino groups. Examples of amido groups include, but are not limited to, —C(=O)NH₂, —C(=O)NHCH₃, —C(=O)N(CH₃)₂, —C(=O)NHCH₂CH₃, and —C(=O)N(CH₂CH₃)₂, as well as amido groups in which R¹ and R², together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR¹R², wherein R¹ and R² are independently amino substituents, as defined for amino groups. Examples of amido groups include, but are not limited to, —C(=S)NH₂, —C(=S)NHCH₃, —C(=S)N(CH₃)₂, and —C(=S)NHCH₂CH₃.

Acylamido (acylamino): —NR¹C(=O)R², wherein R¹ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and R² is an acyl substituent, for example, a $C_{1-7}$alkyl group, a $C_{3-20}$heterocyclyl group, or a $C_{5-20}$aryl group, preferably hydrogen or a $C_{1-7}$alkyl group. Examples of acylamide groups include, but are not limited to, —NHC(=O)CH₃, —NHC(=O)CH₂CH₃, and —NHC(=O)Ph. R¹ and R² may together form a cyclic structure, as in, for example, succinimidyl, maleimidyl, and phthalimidyl:

succinimidyl   maleimidyl   phthalimidyl

Aminocarbonyloxy: —OC(=O)NR¹R², wherein R¹ and R² are independently amino substituents, as defined for amino groups. Examples of aminocarbonyloxy groups include, but are not limited to, —OC(=O)NH₂, —OC(=O)NHMe, —OC(=O)NMe₂, and —OC(=O)NEt₂.

Ureido: —N(R¹)CONR²R³ wherein R² and R³ are independently amino substituents, as defined for amino groups, and R¹ is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCONH₂, —NHCONHMe, —NHCONHEt, —NHCONMe₂, —NHCONEt₂, —NMeCONH₂, —NMeCONHMe, —NMeCONHEt, —NMeCONMe₂, and —NMeCONEt₂.

Guanidino: —NH—C(=NH)NH₂.

Tetrazolyl: a five membered aromatic ring having four nitrogen atoms and one carbon atom, Imino: =NR, wherein R is an imino substituent, for example, for example, hydrogen, a $C_{1-7}$alkyl group, a $C_{3-20}$heterocyclyl group, or a $C_{5-20}$aryl group, preferably H or a $C_{1-7}$alkyl group. Examples of imino groups include, but are not limited to, =NH, =NMe, and =NEt.

Amidine (amidino): —C(=NR)NR₂, wherein each R is an amidine substituent, for example, hydrogen, a $C_{1-7}$alkyl group, a $C_{3-20}$heterocyclyl group, or a $C_{5-20}$aryl group, preferably H or a $C_{1-7}$alkyl group. Examples of amidine groups include, but are not limited to, —C(=NH)NH₂, —C(=NH)NMe₂, and —C(=NMe)NMe₂.

Nitro: —NO₂.

Nitroso: —NO.

Azido: —N₃.

Cyano (nitrile, carbonitrile): —CN.

Isocyano: —NO.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, preferably a $C_{1-7}$alkyl group. Examples of $C_{1-7}$alkylthio groups include, but are not limited to, —SCH₃ and —SCH₂CH₃.

Disulfide: —SS—R, wherein R is a disulfide substituent, for example, a $C_{1-7}$alkyl group, a $C_{3-20}$heterocyclyl group, or a $C_{5-20}$aryl group, preferably a $C_{1-7}$alkyl group (also referred to herein as $C_{1-7}$alkyl disulfide). Examples of $C_{1-7}$alkyl disulfide groups include, but are not limited to, —SSCH₃ and —SSCH₂CH₃.

Sulfine (sulfinyl, sulfoxide): —S(=O)R, wherein R is a sulfine substituent, for example, a $C_{1-7}$alkyl group, a $C_{3-20}$heterocyclyl group, or a $C_{5-20}$aryl group, preferably a $C_{1-7}$alkyl group. Examples of sulfine groups include, but are not limited to, —S(=O)CH₃ and —S(=O)CH₂CH₃.

Sulfone (sulfonyl): —S(=O)₂R, wherein R is a sulfone substituent, for example, a $C_{1-7}$alkyl group, a $C_{3-20}$heterocyclyl group, or a $C_{5-20}$aryl group, preferably a $C_{1-7}$alkyl group, including, for example, a fluorinated or perfluorinated $C_{1-7}$alkyl group. Examples of sulfone groups include, but are not limited to, —S(=O)₂CH₃ (methanesulfonyl, mesyl), —S(=O)₂CF₃ (triflyl), —S(=O)₂CH₂CH₃ (esyl), —S(=O)₂ C₄F₉ (nonaflyl), —S(=O)₂CH₂CF₃ (tresyl), —S(=O)₂ CH₂CH₂NH₂ (tauryl), —S(=O)₂Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO₂H.

Sulfonic acid (sulfo): —S(=O)₂OH, —SO₃H.

Sulfinate (sulfinic acid ester): —S(=O)OR; wherein R is a sulfinate substituent, for example, a $C_{1-7}$alkyl group, a $C_{3-20}$heterocyclyl group, or a $C_{5-20}$aryl group, preferably a $C_{1-7}$alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$alkyl group, a $C_{3-20}$heterocyclyl group, or a $C_{5-20}$aryl group, preferably a $C_{1-7}$alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$alkyl group, a $C_{3-20}$heterocyclyl group, or a $C_{5-20}$aryl group, preferably a $C_{1-7}$alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$alkyl group, a $C_{3-20}$heterocyclyl group, or a $C_{5-20}$aryl group, preferably a $C_{1-7}$alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$alkyl group, a $C_{3-20}$heterocyclyl group, or a $C_{5-20}$aryl group, preferably a $C_{1-7}$alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$alkyl group, a $C_{3-20}$heterocyclyl group, or a $C_{5-20}$aryl group, preferably a $C_{1-7}$alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$alkyl group, a $C_{3-20}$heterocyclyl group, or a $C_{5-20}$aryl group, preferably a $C_{1-7}$alkyl group or a $C_{5-20}$aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$^2$$_2$, where R$^1$ and R$^2$ are phosphoramidite substituents, for example, —H, a (optionally substituted)$C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$^2$$_2$, where R$^1$ and R$^2$ are phosphoramidate substituents, for example, —H, a (optionally substituted)$C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Silyl: —SiR$_3$, where R is a silyl substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of silyl groups include, but are not limited to, —SiH$_3$, —SiH$_2$(CH$_3$), —SiH(CH$_3$)$_2$, —Si(CH$_3$)$_3$, —Si(Et)$_3$, —Si(iPr)$_3$, —Si(tBu)(CH$_3$)$_2$, and —Si(tBu)$_3$.

Oxysilyl: —Si(OR)$_3$, where R is an oxysilyl substituent, for example, —H, a $C_{1-7}$alkyl group, a $C_{3-20}$heterocyclyl group, or a $C_{5-20}$aryl group, preferably —H, a $C_{1-7}$alkyl group, or a $C_{5-20}$aryl group. Examples of oxysilyl groups include, but are not limited to, —Si(OH)$_3$, —Si(OMe)$_3$, —Si(OEt)$_3$, and —Si(OtBu)$_3$.

Siloxy (silyl ether): —OSiR$_3$, where SiR$_3$ is a silyl group, as discussed above.

Oxysiloxy: —OSi(OR)$_3$, wherein OSi(OR)$_3$ is an oxysilyl group, as discussed above.

In many cases, substituents are themselves substituted.

For example, a $C_{1-7}$alkyl group may be substituted with, for example:

hydroxy (also referred to as a hydroxy-$C_{1-7}$alkyl group);
halo (also referred to as a halo-$C_{1-7}$alkyl group);

amino (also referred to as a amino-$C_{1-7}$alkyl group);
carboxy (also referred to as a carboxy-$C_{1-7}$alkyl group);
$C_{1-7}$alkoxy (also referred to as a $C_{1-7}$alkoxy-$C_{1-7}$alkyl group);
$C_{5-20}$aryl (also referred to as a $C_{5-20}$aryl-$C_{1-7}$alkyl group).

Similarly, a $C_{5-20}$aryl group may be substituted with, for example:
hydroxy (also referred to as a hydroxy-$C_{5-20}$aryl group);
halo (also referred to as a halo-$C_{5-20}$aryl group);
amino (also referred to as an amino-$C_{5-20}$aryl group, e.g., as in aniline);
carboxy (also referred to as an carboxy-$C_{5-20}$aryl group, e.g., as in benzoic acid);
$C_{1-7}$alkyl (also referred to as a $C_{1-7}$alkyl-$C_{5-20}$aryl group, e.g., as in toluene);
$C_{1-7}$alkoxy (also referred to as a $C_{1-7}$alkoxy-$C_{5-20}$aryl group, e.g., as in anisole);
$C_{5-20}$aryl (also referred to as a $C_{5-20}$aryl-$C_{5-20}$aryl, e.g., as in biphenyl).

These and other specific examples of such substituted-substituents are described below.

Hydroxy-$C_{1-7}$alkyl: The term "hydroxy-$C_{1-7}$alkyl," as used herein, pertains to a $C_{1-7}$alkyl group in which at least one hydrogen atom (e.g., 1, 2, 3) has been replaced with a hydroxy group. Examples of such groups include, but are not limited to, —$CH_2OH$, —$CH_2CH_2OH$, and —$CH(OH)CH_2OH$.

Halo-$C_{1-7}$alkyl group: The term "halo-$C_{1-7}$alkyl," as used herein, pertains to a $C_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a $C_{1-7}$perhaloalkyl group." Examples of such groups include, but are not limited to, —$CF_3$, —$CHF_2$, —$CH_2F$, —$CCl_3$, —$CBr_3$, —$CH_2CH_2F$, —$CH_2CHF_2$, and —$CH_2CF_3$.

Amino-$C_{1-7}$alkyl: The term "amino-$C_{1-7}$alkyl," as used herein, pertains to a $C_{1-7}$alkyl group in which at least one hydrogen atom (e.g., 1, 2, 3) has been replaced with an amino group. Examples of such groups include, but are not limited to, —$CH_2NH_2$, —$CH_2CH_2NH_2$, and —$CH_2CH_2N(CH_3)_2$.

Carboxy-$C_{1-7}$alkyl: The term "carboxy-$C_{1-7}$alkyl," as used herein, pertains to a $C_{1-7}$alkyl group in which at least one hydrogen atom (e.g., 1, 2, 3) has been replaced with a carboxy group. Examples of such groups include, but are not limited to, —$CH_2COOH$ and —$CH_2CH_2COOH$.

$C_{1-7}$alkoxy-$C_{1-4}$alkyl: The term "$C_{1-7}$alkoxy-$C_{1-7}$alkyl," as used herein, pertains to a $C_{1-7}$alkyl group in which at least one hydrogen atom (e.g., 1, 2, 3) has been replaced with a $C_{1-7}$alkoxy group. Examples of such groups include, but are not limited to, —$CH_2OCH_3$, —$CH_2CH_2OCH_3$, and, —$CH_2CH_2OCH_2CH_3$ $C_{5-20}$aryl-$C_{1-7}$alkyl: The term "$C_{5-20}$aryl-$C_{1-7}$alkyl," as used herein, pertains to a $C_{1-7}$alkyl group in which at least one hydrogen atom (e.g., 1, 2, 3) has been replaced with a $C_{5-20}$aryl group. Examples of such groups include, but are not limited to, benzyl (phenylmethyl, $PhCH_2$—), benzhydryl ($Ph_2CH$—), trityl (triphenylmethyl, $Ph_3C$—), phenethyl (phenylethyl, Ph-$CH_2CH_2$—), styryl (Ph-CH=CH—), cinnamyl (Ph-CH=CH—$CH_2$—).

Hydroxy-$C_{5-20}$aryl: The term "hydroxy-$C_{5-20}$aryl," as used herein, pertains to a $C_{5-20}$aryl group in which at least one hydrogen atom (e.g., 1, 2, 3) has been substituted with an hydroxy group. Examples of such groups include, but are not limited to, those derived from: phenol, naphthol, pyrocatechol, resorcinol, hydroquinone, pyrogallol, phloroglucinol.

Halo-$C_{5-20}$aryl: The term "halo-$C_{5-20}$aryl," as used herein, pertains to a $C_{5-20}$aryl group in which at least one hydrogen atom (e.g., 1, 2, 3) has been substituted with a halo (e.g., F, Cl, Br, I) group. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

$C_{1-7}$alkyl-$C_{5-20}$aryl: The term "$C_{1-7}$alkyl-$C_{5-20}$aryl," as used herein, pertains to a $C_{5-20}$aryl group in which at least one hydrogen atom (e.g., 1, 2, 3) has been substituted with a $C_{1-7}$alkyl group. Examples of such groups include, but are not limited to, tolyl (from toluene), xylyl (from xylene), mesityl (from mesitylene), and cumenyl (or cumyl, from cumene), and duryl (from durene).

Hydroxy-$C_{1-7}$alkoxy: —OR, wherein R is a hydroxy-$C_{1-7}$alkyl group. Examples of hydroxy-$C_{1-7}$alkoxy groups include, but are not limited to, —$OCH_2OH$, —$OCH_2CH_2OH$, and —$OCH_2CH_2CH_2OH$.

Halo-$C_{1-7}$alkoxy: —OR, wherein R is a halo-$C_{1-7}$alkyl group. Examples of halo-$C_{1-7}$alkoxy groups include, but are not limited to, —$OCF_3$, —$OCHF_2$, —$OCH_2F$, —$OCCl_3$, —$OCBr_3$, —$OCH_2CH_2F$, —$OCH_2CHF_2$, and —$OCH_2CF_3$.

Carboxy-$C_{1-7}$alkoxy: —OR, wherein R is a carboxy-$C_{1-7}$alkyl group. Examples of carboxy-$C_{1-7}$alkoxy groups include, but are not limited to, —$OCH_2COOH$, —$OCH_2CH_2COOH$, and —$OCH_2CH_2CH_2COOH$.

$C_{1-7}$alkoxy-$C_{1-7}$alkoxy: —OR, wherein R is a $C_{1-7}$alkoxy-$C_{1-7}$alkyl group. Examples of $C_{1-7}$alkoxy-$C_{1-7}$alkoxy groups include, but are not limited to, —$OCH_2OCH_3$, —$OCH_2CH_2OCH_3$, and —$OCH_2CH_2OCH_2CH_3$.

$C_{5-20}$aryl-$C_{1-7}$alkoxy: —OR, wherein R is a $C_{5-20}$aryl-$C_{1-7}$alkyl group. Examples of such groups include, but are not limited to, benzyloxy, benzhydryloxy, trityloxy, phenethoxy, styryloxy, and cimmamyloxy.

$C_{1-7}$alkyl-$C_{5-20}$aryloxy: —OR, wherein R is a $C_{1-7}$alkyl-$C_{5-20}$aryl group. Examples of such groups include, but are not limited to, tolyloxy, xylyloxy, mesityloxy, cumenyloxy, and duryloxy.

Amino-$C_{1-7}$alkyl-amino: The term "amino-$C_{1-7}$alkyl-amino," as used herein, pertains to an amino group, —$NR^1R^2$, in which one of the substituents, $R^1$ or $R^2$, is itself a amino-$C_{1-7}$alkyl group (—$C_{1-7}$alkyl-$NR^3R^4$). The amino-$C_{1-7}$alkylamino group may be represented, for example, by the formula —$NR^1$—$C_{1-7}$alkyl-$NR^3R^4$. Examples of such groups include, but are not limited to, groups of the formula —$NR^1$$(CH_2)_n NR^1R^2$, where n is 1 to 6 (for example, —$NHCH_2NH_2$, —$NH(CH_2)_2NH_2$, —$NH(CH_2)_3NH_2$, —$NH(CH_2)_4NH_2$, —$NH(CH_2)_5NH_2$, —$NH(CH_2)_6NH_2$), —$NHCH_2NH(Me)$, —$NH(CH_2)_2NH(Me)$, —$NH(CH_2)_3NH(Me)$, —$NH(CH_2)_4NH(Me)$, —$NH(CH_2)_5NH(Me)$, —$NH(CH_2)_6NH(Me)$, —$NHCH_2NH(Et)$, —$NH(CH_2)_2NH(Et)$, —$NH(CH_2)_3NH(Et)$, —$NH(CH_2)_4NH(Et)$, —$NH(CH_2)_5NH(Et)$, and —$NH(CH_2)_6NH(Et)$.

DETAILED DESCRIPTION OF THE INVENTION

Sensor Preparation

A sensor of the invention was prepared using poly(histidine) as the sensor and fluorescein as the probe group.

Experimental Details 5 mg of poly-histidine was dissolved in 2.5 ml of carbonate buffer pH 9 solution. FITC (fluorescein isothiocyanate) was dissolved in anhydrous DMSO at a concentration of 1 mg/ml.

For each ml of poly-histidine solution, 50 μl of FITC solution was added to the poly-histidine solution. The addition was performed very slowly in 5 μl aliquots, while gently and continuously stirring the solution. Total volume now 2.65 ml. After all the required amount of FITC solution has been added, the mixture was incubated in the dark for 8 hours at 4° C. Ammonium chloride was added to a final concentration of 50 mM (7 mg) and incubated for a further 2 hours at 4° C. Distilled water was added to the mixture to a total volume of 10 ml. The mixture was dialysed against the distilled water overnight. 1 ml aliquots of the above solution was kept in suitable containers wrapped in foil in the freezer as stock solutions.

The reaction product was characterised using gel permeation chromatography, BioRad P2 or equivalent size exclusion matrix, and monitored at 495 nm absorption wavelength.

Example 1

Superalloy Rod Testing

Figure 1A:
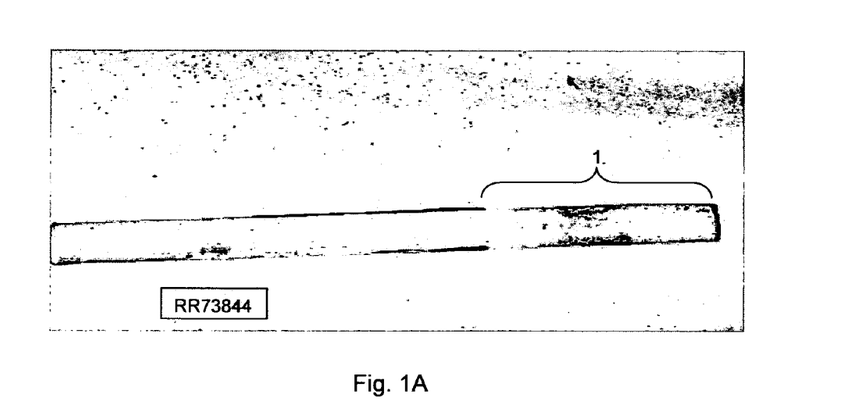

FIG. 1A shows RR73844 rod after a 1 cm portion of the rod (labelled 1) has been immersed immersion in peroxide solution for 24 hours and then the whole rod has been immersed in chemical sensor solution for 24 hours. In the figures, dark areas represent areas where fluorescence has been observed with the excitation laser and observation filter. White areas correspond to regions where no fluorescence has been observed.

Figure 1B:
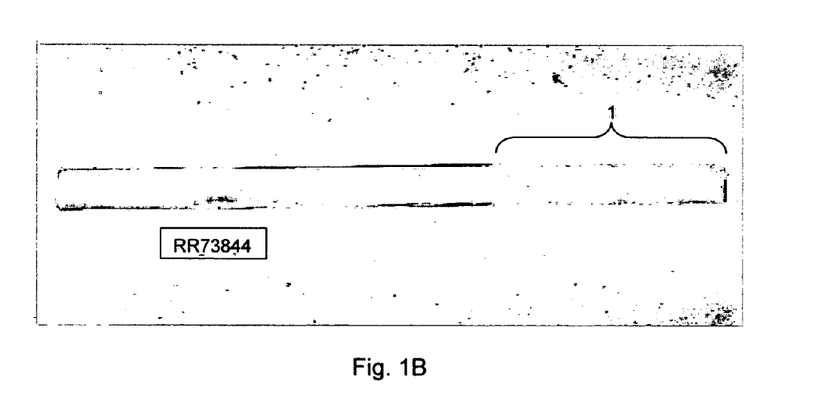

The right-hand side of FIG. 1A (labelled 1) shows a darker region that correlates with exposure to peroxide. Further left a lighter region is present, which was not exposed to peroxide. FIG. 1B shows a fluorescence image of the same rod after it has been wiped with acetic acid. None of the chemical sensor remains and the oxidised region is once again invisible against the rest of the metal.

Figure 2A:
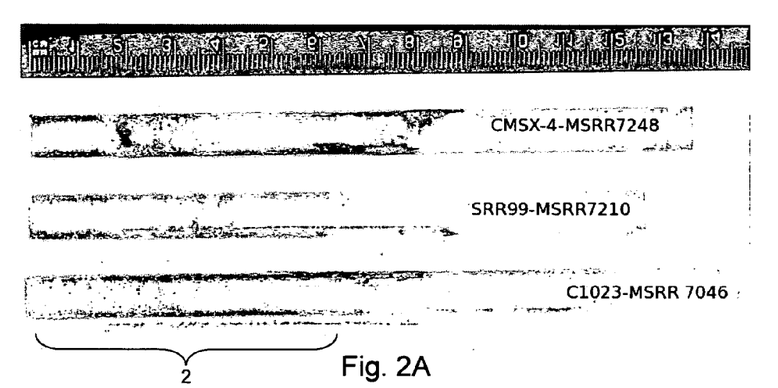
Figure 2B:
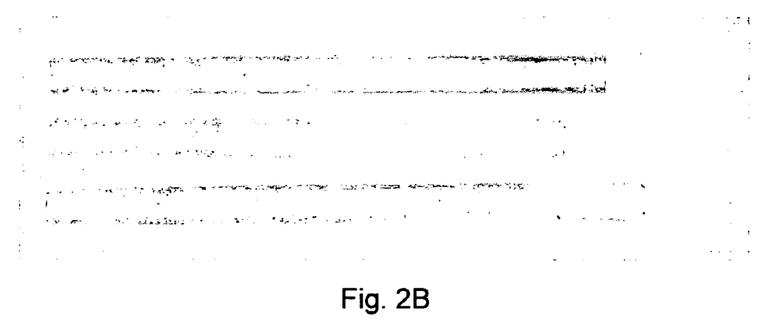

FIG. 2A shows the result from exposing superalloy rods CMSX®-4, SRR99 and C1023 to peroxide and the sensor, and imaged using an excitation laser and a camera fitted with an observation filter. In this figure, the area exposed to peroxide is shown to the left of the figure (labelled 2). A variety of lighter and darker regions can be seen. For example, the area exposed to peroxide on the CMSX®-4 rod was darker in fluorescence than the rest of the rod.

Experimental Details

The superalloy rods were supplied in a cylindrical form about 10 cm long and 1 cm in diameter. Part of each had been skimmed to remove the surface coating and expose the fresh superalloy surface. Over a fortnight had elapsed between skimming and experimental testing.

Rod RR73844 is composed of superalloy MAR-M-002, which is a cast nickel based super alloy with a nominal chemical composition: 10.1Co, 9.9W, 8.9Cr, 5.8Al, 2.5Ta, 1.5Ti, 1.5Hf, 0.1Mo, 0.03Zr, 0.13C, Balance Ni.

The end (1 cm) of exposed rod was submerged in 20% v/v hydrogen peroxide solution for 24 hours and the rod was washed, dried and placed in the chemical sensor solution (in HEPES buffered pH 7.2) for a further 24 hours. The rods was washed extensively in HEPES buffer pH 7.2, air dried and scanned for fluorescence on a flatbed scanner.

Images were produced using a flat-bed laser scanner (both the laser and camera operated from below the sample, which was placed an a transparent glass surface). The laser was an argon ion type with an emission wavelength of 488 nm and the camera was a charge-coupled device with a 526 nm filter.

After imaging the rod was wiped with 20% v/v acetic acid to remove the sensor reimaged (FIG. 1B).

The three further superalloy rods were made from the following alloys: CMSX-4, SRR99 and C1023.

CMSX®4 nominal composition: 9.6 Co, 6.5 Cr, 6.5 Ta, 6.4 W, balance Ni.

SRR99 nominal composition: 9.5 W, 8.5 Cr, 5.5 Al, 5 Co, 2.8 Ta, balance Ni.

C1023 nominal composition: 15.5 Cr, 9.7 Co, 8.3 Mo, 4.1 Al, balance Ni.

Each rod was subjected to peroxide solution for 24 hours (the end 1 cm), washed and then immersed in chemical sensor solution, as before.

As before, each rod was cleaned with acetic acid and reimaged by fluorescence to show that the features were observed due to fluorescence.

Example 2

Turbine Superalloy Testing

Figure 3A:
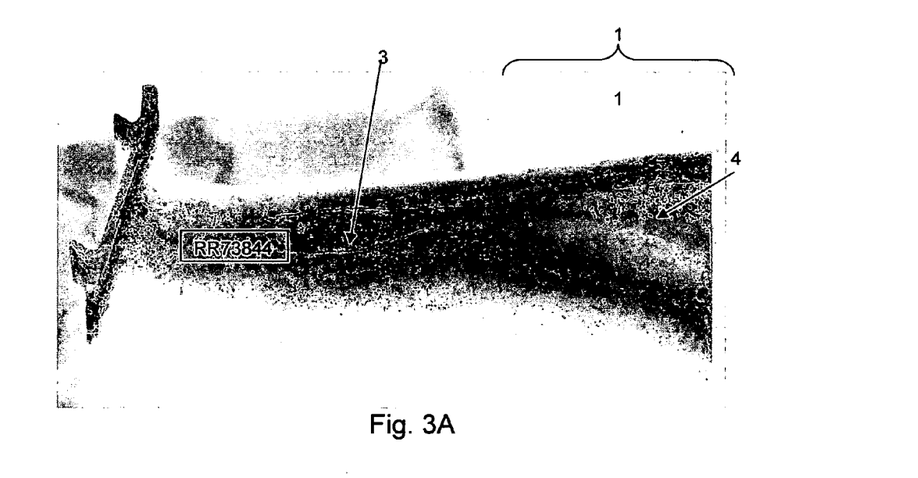

FIG. 3A shows a service-run HP (High Pressure) turbine blade from a Trent® 900 engine. The blade has been cross sectioned at points 3 and 4, in order to expose the Ni superalloy through the Pt coating. The blade was immersed in chemical sensor for 24 hours, washed with water and fluorescence imaged, as above.

Figure 3B:
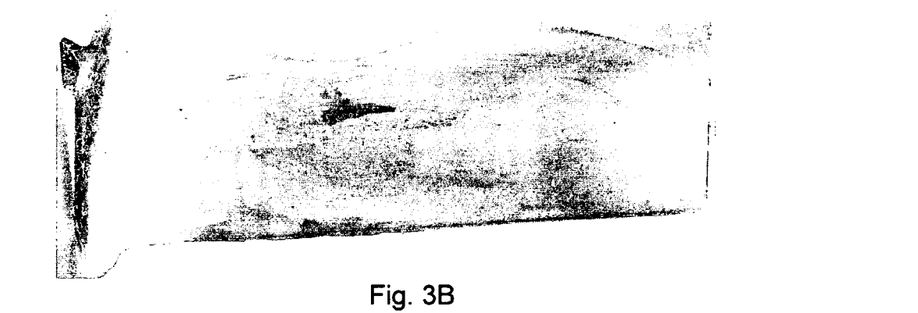

A complex array of spots and dark areas are revealed by the chemical sensor, which are not visible on normal inspection. Also, there is evidence that some of the regions where the surface has been ground away have a higher fluorescence response. For comparison, FIG. 3B shows the same turbine blade using fluorescence imaging after removal of the chemical sensor with acetic acid. Very few features are visible in this image, indicating that the chemical sensor is able to selectively associate with certain areas.

From Example 1, we note that the sensor associates with transition metals in an oxidation state greater than zero. In FIG. 3A, the dark areas show the distribution of the sensor and thus the areas of transition metals in an oxidation state greater than zero. These areas correlate to areas of degradation of the alloy surface.

Cut away sections 3 and 4 shows a large, mostly homogenous area of degradation. In contrast, in areas that have not been cut away, small circular areas of sensor.

Experimental Details

A service-run HP turbine blade from a Trent® 900 engine was cross sectioned. The blade was immersed in chemical sensor for 24 hours, washed with water and fluorescence imaged, as above.

The invention claimed is:

1. A method of determining the distribution of degradation of a vehicle component previously exposed to degradation conditions during use, the vehicle component including a surface layer of an alloy comprising a first transition metal in a first oxidation state and a second transition metal in a second oxidation state different from the first oxidation state, wherein the first and second transition metals are the same or different transition metal elements, the method comprising the step of:

(i) applying to the surface layer of the vehicle component a first oxidation state sensor molecule that selectively binds to the first transition metal in the first oxidation state and not with the second transition metal in the second oxidation state, wherein the first oxidation state sensor molecule includes an oxidation state discriminating group and a probe group attached to the oxidation state discriminating group, such that the oxidation state discriminating group selectively binds to the first transition metal, and the probe group includes a luminescent or radioactive group effective to emit an observable signal; and (ii) observing the surface of the alloy to determine the location of the first oxidation state sensor molecule associated with the first transition metal in the first oxidation state.

2. The method according to claim 1, wherein the first oxidation state is greater than zero and the second oxidation state is zero.

3. The method according to claim 1, wherein the sensor comprises a plurality of oxidation state discriminating groups.

4. The method according to claim 1, wherein the first transition metal element is the same as the second transition metal element.

5. The method according to claim 1, wherein the alloy is a superalloy.

6. The method according to claim 1, wherein the alloy is a single crystal metal alloy or a polycrystalline alloy.

7. The method according to claim 1, wherein the sensor is applied to the surface as an aqueous solution.

8. A method according to claim 1, wherein said surface layer of said alloy comprises a transition metal, a first transition metal in a first oxidation state, a second transition metal in a second oxidation state different from the first oxidation state and a third transition metal in a third oxidation state different from the first and second oxidation states, and wherein the method additionally comprises the step of:
applying a second oxidation state sensor molecule to a second portion of the surface of the alloy, wherein the second oxidation state sensor molecule selectively binds to the third transition metal, such the distribution of the second oxidation state sensor molecule can be used to discriminate between the first, second and third transition metals.

9. The method according to claim 1, wherein the alloy is part of an aircraft component.

10. The method according to claim 9, wherein the aircraft component is selected from a turbine blade, an engine casing and an aerofoil.

11. The method according to claim 1, wherein the oxidation state discriminating group comprises a Lewis base group, which Lewis base group is a heterocyclic group and comprises an atom selected from the group consisting of N, O and S.

12. The method according to claim 11, wherein the heterocyclic group is selected from a group consisting of pyrrole, imidazole, pyrazole, oxazole, thiaozle, pyridine, pyridazine, pyrimidine and pyrazine.

13. The method according to claim 1, wherein the probe group comprises a fluorophore.

14. The method according to claim 13, wherein said fluorophore is a fluorescein or a fluorescein derivative.

15. The method according to claim 1, wherein the first transition metal is selected from the group consisting of Ni(II), Ni(III), Co(II), Co(III), Fe(II), Fe(III), Fe(V), Cu(I) and Cu(II).

16. The method according to claim 15, wherein the second transition metal is selected from the group consisting of Ni(0), Co(0), Fe(0) and Cu(0).

17. The method according to claim 1, the method further comprising the step of:
(iii) removing excess oxidation state sensor molecules from the surface of the alloy.

18. The method according to claim 17, further comprising the step of:
(iv) observing a signal from the sensor on the surface of the alloy by an imaging means.

19. The method according to claim 18, further including the step of:
(v) removing the oxidation state sensor molecule from the alloy surface by washing the surface with an aqueous acid solution.

20. The method according to claim 17, wherein said modifying step modifies the surface of the alloy to include a probe group comprising a fluorophore.

21. A method of determining the distribution of degradation of a vehicle component previously exposed to degradation conditions during use, the vehicle component including a surface layer of an alloy comprising a first transition metal in a first oxidation state and a second transition metal in a second oxidation state different from the first oxidation state, wherein the first and transition metals are the same or different transition metal elements, and wherein an oxidation state sensor molecule is selectively bound to the first transition metal, wherein the first oxidation state sensor molecule includes an oxidation state discriminating group that selectively binds to the first transition metal, the method comprising the step of:
(i) modifying the oxidation state sensor molecule on the surface of the alloy by attaching a probe group to the oxidation state discriminating group, the probe group including luminescent or radioactive group effective to emit an observable signal,
such that the distribution of the modified oxidation state sensor molecule on the surface can be used to discriminate between the first and second transition metals.

22. A method of determining the distribution of degradation of a vehicle component previously exposed to degradation conditions during use, the vehicle component including a surface layer comprising an alloy comprising a first transition metal in a first oxidation state and a second transition metal of a second oxidation state different from the first oxidation state, wherein the first and second transition metals are the same or different transition metal elements, and an oxidation state sensor molecule is selectively bound to the first transition metal, wherein the first oxidation state sensor molecule includes an oxidation state discriminating group and a probe group attached to the oxidation state discriminating group, such that the oxidation state discriminating group selectively binds to the first transition metal, and the probe group includes a luminescent or radioactive group effective to emit an observable signal, the method comprising the step of:
(i) observing the oxidation state sensor molecule on the surface of the alloy and using the distribution of the sensor molecule to discriminate between the first and second transition metals.

* * * * *